United States Patent
Ramirez et al.

(10) Patent No.: US 10,252,088 B2
(45) Date of Patent: *Apr. 9, 2019

(54) TOPICAL COMPOSITIONS AND METHODS OF MANUFACTURING THEM IN SPECIFICALLY TREATED STEEL VESSELS

(71) Applicant: Obagi Cosmeceuticals LLC, Long Beach, CA (US)

(72) Inventors: Jose E. Ramirez, Trumball, CT (US); Austin McNamara, Villa Park, CA (US); Judy Hattendorf, Marina Del Rey, CA (US); Steve Goldner, Farmington Hills, MI (US)

(73) Assignee: Obagi Cosmeceuticals LLC, Long Beach, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/942,445

(22) Filed: Jul. 15, 2013

(65) Prior Publication Data

US 2014/0161746 A1 Jun. 12, 2014

Related U.S. Application Data

(63) Continuation of application No. 11/291,453, filed on Dec. 1, 2005, now abandoned.

(60) Provisional application No. 60/632,438, filed on Dec. 2, 2004.

(51) Int. Cl.
*A61K 8/02* (2006.01)
*A61K 8/34* (2006.01)
*A61Q 19/02* (2006.01)
*A61K 8/365* (2006.01)

(52) U.S. Cl.
CPC .............. *A61Q 19/02* (2013.01); *A61K 8/347* (2013.01); *A61K 8/365* (2013.01); *A61K 2800/26* (2013.01); *A61K 2800/87* (2013.01)

(58) Field of Classification Search
CPC .... A61K 8/347; A61K 8/365; A61K 2800/87; A61K 2800/26; A61Q 19/02
See application file for complete search history.

(56) References Cited

U.S. PATENT DOCUMENTS

| | | |
|---|---|---|
| 2,376,884 A | 5/1945 | Schwenk |
| 2,377,188 A | 5/1945 | Schwenk |
| 3,755,560 A | 8/1973 | Dickert |
| 3,856,934 A | 12/1974 | Kligman |
| 3,890,165 A * | 6/1975 | Liao .............................. 148/250 |
| 4,136,166 A | 1/1979 | Barnett |
| 4,229,427 A | 10/1980 | Whitehouse |
| 4,421,769 A | 12/1983 | Dixon |
| 4,466,955 A | 8/1984 | Calvo |
| 4,526,779 A | 7/1985 | Hashimoto |
| 4,792,443 A | 12/1988 | Filomeno |
| 5,143,763 A | 9/1992 | Yamada |
| 5,523,077 A | 6/1996 | Pawelek |
| 5,621,006 A | 4/1997 | Yu |
| 5,780,086 A * | 7/1998 | Kirksey et al. ............ 426/330.3 |
| 5,961,961 A * | 10/1999 | Dobkowski et al. ........... 424/59 |
| 6,265,363 B1 * | 7/2001 | Viscovitz ................. A61K 8/22 510/130 |
| 6,497,860 B1 | 12/2002 | Kawato |
| 6,699,464 B1 | 3/2004 | Popp |
| 7,282,493 B2 | 10/2007 | Adams |
| 2003/0053968 A1 * | 3/2003 | Wortzman ............... A61K 8/23 424/62 |
| 2004/0052741 A1 | 3/2004 | Wortzman |
| 2004/0185016 A1 | 9/2004 | Popp |

FOREIGN PATENT DOCUMENTS

| | | |
|---|---|---|
| EP | 0688204 B1 | 12/1995 |
| WO | 01/85102 A2 | 11/2001 |

OTHER PUBLICATIONS

Kremer, Lee. "Citric Acid Passivation of Stainless Steel." Retrieved from URL: https://www.pfonline.com/articles/citric-acid-passivation-of-stainless-steel; May 1, 1999, pp. 1-3.*
1995 U.S. Pharmacopeia/National Formulary USP 23/NF 18, pp. 769-770 and 1572-1573.
"Hydroquinone" Merck Index, 12th edition, edited by Susan Budavari, 1996, monograph 4853, p. 825.
Alster, "Combined laser resurfacing and tretinoin treatment of facial rhytides," Cosmetic Dermatology, vol. 10, No. 11, pp. 39-42 (Nov. 1997).
Brochure—The Science of Skin Health Restoration, Nu-Derm System (2000).
Buka et al., "How to use retinoids to prevent skin cancer and treat photoaging," Skin & Aging, pp. 32-39 (Jun. 1999).
*Cosmetic/Personal Care Packaging. Containers.* http://www.cpcpkg.com. Oct. 22, 2004.
Green et al., "Photoaging and the skin," Dermatologic Clinics, vol. 11, No. 1, pp. 97-105 (Jan. 1993).
Insert—Obagi Medical Products, Inc., Long Beach, CA 90502 (2000).
Lowe, "Understanding how topical retinoids work," Skin & Aging, pp. 39-42 (Feb. 1999).
Olsen et al., "Tretinoin emollient cream for photodamaged skin: Results of 48-week, multicenter, double-blind studies," Journal of the American Academy of Dermatology, pp. 217-226 (Aug. 1997).
Photo of Obagi Nu-Derm™ Action™, front and back images (1999).

(Continued)

*Primary Examiner* — Doan T Phan
(74) *Attorney, Agent, or Firm* — Kilpatrick Townsend & Stockton LLP

(57) ABSTRACT

Stable hydroquinone compositions that are useful for skin care and can have a shelf life of up to three years are prepared in a tank made from a material that does not release metallic ions into the composition.

22 Claims, No Drawings

(56) References Cited

OTHER PUBLICATIONS

Photo of Obagi Nu-Derm™ Cleanser II™, front and back images (1997).
Photo of Obagi Nu-Derm™ Clear™, front and back images (1997).
Photo of Obagi Nu-Derm™ Exfoderm™, front and back images (1997).
Photo of Obagi Nu-Derm™ Toner II™, front and back images (1995).
Photo of Obagi Nu-Derm™ Toner I™, back image (1997).

* cited by examiner

TOPICAL COMPOSITIONS AND METHODS OF MANUFACTURING THEM IN SPECIFICALLY TREATED STEEL VESSELS

CROSS REFERENCE TO RELATED APPLICATIONS

This application is a continuation of U.S. application Ser. No. 11/291,453, filed Dec. 1, 2005, which claims priority benefit of U.S. Provisional Application No. 60/632,438 filed Dec. 2, 2004, the entire disclosure of which is incorporated herein by this reference.

BACKGROUND

Technical Field

The present disclosure relates to stable skin care compositions containing hydroquinone, chelating agents and methods for manufacturing them in specially treated steel vessels.

Background of the Invention

Hydroquinone inhibits the formation of melanin and pigmentation of the skin and, accordingly, has been found to be useful in skin care products, especially products designed to lighten the skin of a user. Unfortunately, hydroquinone compositions turn to a brown color as the hydroquinone in the composition is oxidized. The discoloration of the hydroquinone product is aesthetically undesirable and unacceptable to the consumer. Also, the oxidation by-products of hydroquinone may diminish its effectiveness and irritate the skin of a user.

Although various attempts have been made to solve the problem of discoloration of hydroquinone skin care compositions, applicants are unaware of any stabilized composition that provides the three year shelf-life that is desirable for consumer skin care products. Thus, there remains room for improvement in manufacturing hydroquinone skin care compositions, especially to provide hydroquinone skin care compositions that do not oxidize and discolor during shipment and storage and which exhibit a three year shelf-life.

SUMMARY

Methods for preparing stable hydroquinone compositions are described herein. The methods include the steps of preparing an emulsion by adding an oil phase to an aqueous phase. Both phases are prepared in and admixed in vessels that do not release ions into the composition. In embodiments, the vessels are stainless steel vessels (of grade 316 or higher) that have been previously treated and passivated with a chelating acid such as citric acid solution.

DETAILED DESCRIPTION OF PREFERRED EMBODIMENTS

The present disclosure relates to methods for making stable hydroquinone-containing compositions for skin care. As used herein the term "stable" means that the composition when in a closed container remains within the tolerances and limits set forth in US Pharmacopeia and/or the US FDA guidelines or monographs for compositions containing hydroquinone (or hydroquinone in combination with one or more other active ingredients). The entire US Pharmacopeia and collection of US FDA guidelines or monographs for compositions containing any particular active ingredient or combination of active ingredients are too voluminous to present in their entirety herein and thus are instead incorporated in their entirety by this reference. With respect to topical compositions, the tolerances and limits are frequently presented relative to the labeled amount. With respect to hydroquinone cream, for example, the acceptable tolerance is not less than 94.0 percent and not more than 106.0 percent of the labeled amount of $C_6H_6O_2$. Those skilled in the art will readily be able to identify the tolerances and limits for other compositions containing hydroquinone.

Stability of the present compositions can be evaluated through accelerated stability studies. In these tests, the packaged composition is maintained at an elevated temperature for a period of time after which it is examined. The exposure to elevated temperatures for a given period correlates to a correspondingly longer period of time at room temperature. Thus, for example, if a product remains within the required tolerances and limits when maintained for a period of 12 weeks at a temperature of 40° C. and 12 months further at room temperature, one can conclude that the product has a shelf life of greater than two and up to three years at room temperature. Those skilled in the art will envision other testing to confirm the stability of the products described herein. Further testing methodology is described in the working examples below.

As those skilled in the art will appreciate, the container-liner-closure system used to store the composition will affect the stability of the active ingredient. It should be understood that a composition need not be stable in all containers to be stable in accordance with this disclosure. Stability in at least one type of container is sufficient for a composition to be stable as that term is used herein.

In particularly useful embodiments, hydroquinone compositions in accordance with the present disclosure can be stable for at least three years at room temperature. Compositions in accordance with some embodiments of this disclosure can be effective in reducing melanin, inhibiting tyrosine, destroying melanocytes, and are thus may be useful as skin lightening compositions.

The hydroquinone compositions of the present disclosure contain hydroquinone and a unique mixture of ingredients and includes an aqueous phase and an oil phase. Hydroquinone is a well-known compound having the general formula:

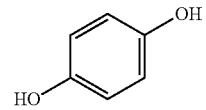

The hydroquinone is present in amounts that provide a benefit to the skin of a user. In embodiments, hydroquinone is present in an amount sufficient to effect depigmentation. Generally, hydroquinone in amounts from about 0.1 to about 10% by weight of the total composition is suitable. In embodiments, hydroquinone is present in an amount from about 1 to about 5% by weight of the total composition. In yet other embodiments, hydroquinone is present in an amount from about 2.5 to about 4.5% by weight of the total composition.

The aqueous phase includes water, humectants, emulsifiers, preservatives, chelating agents, reducing agents and a pH adjuster. Purified water can advantageously be used, such as, for example, de-ionized water or USP water.

Suitable preservatives for the aqueous phase include, but are not limited to methylparaben, sodium butylparaben, benzoic acid and its salts and esters, benzyl alcohol, urea derivatives such as diazolidinyl urea, imidazolidinyl urea, and DMDM hydantoin, sorbic acid and its salts, and the like. Typically, the preservatives are present in an amount from about 0.01 to about 5% by weight of the total composition. In embodiments, the preservatives are present in an amount from about 0.05 to about 1% by weight of the total composition.

Suitable chelating agents for the use in the aqueous phase include, but are not limited to edetate disodium, EDTA (ethylenediaminetetraacetic acid) and its salts, for example, trisodium NTA (nitrilotriacetic acid), etidronic acid and its salts, sodium dihydroxyethylglycinate, citric acid and its salts, and combinations thereof. Typically, the amount of chelating agent(s) is from about 0.01 to about 5% by weight of the total composition. In embodiments, the chelating agents are present in an amount of about 0.05 to about 1% by weight of the total composition.

Suitable humectants for use in the aqueous phase include, but are not limited to polyhydric alcohols including glycerin, diglycerin, triglycerin, polyglycerin, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, ethylene glycol monoalkyl ether, diethylene glycol monoalkyl ether, glucose, maltose, sucrose, lactose, xylitose, xylitol, sorbitol, mannitol, maltitol, panthenol, pentaerythritol, and hyaluronic acid and its salts. It should, of course be understood that combinations of two or more humectants can be included in the present compositions. Typically, humectants are present in an amount from about 1 to about 20% by weight of the total composition. In embodiments, humectants are present in an amount from about 2 to about 5% by weight of the total composition.

Suitable emulsifiers for use in the aqueous phase are surfactants. Useful surfactants can be ionic or nonionic, and they can be used alone or in admixture. Illustrative examples of suitable surfactants include cetearyl alcohol and sodium cetearyl sulfate, PEG-1000 monocetyl ether, or quaternary ammonium salts such as alkyl trimethyl ammonium bromide; polyol ester glycerol monostearate and potassium stearate, sodium lauryl sulfate (SLS), and ethoxylated fatty alcohols constitute good coemulsifiers. Fatty acids like stearic acids may be included to regulate the consistency of the emulsion. Optionally, polymers such as carbomers also can be included. Particularly useful emulsifiers for use in the aqueous phase are sodium lauryl sulfate, saponins or combinations thereof. Typically, the emulsifiers are present in an amount from about 1 to about 20% by weight of the total composition. In embodiments, the emulsifiers are present in an amount from about 2 to about 5% by weight of the total composition.

The pH of the aqueous phase can be adjusted to be between about 2 to 4, such that the final product has a pH such as between about 2 to 4. Agents suitable for adjusting the pH of the aqueous phase include, but are not limited to citric acid, phosphoric acid, lactic acid or glycolic acid. Typically, the pH adjustment agents are present in an amount from about 0.01 to about 5% by weight of the total composition. In embodiments, the pH adjustment agent is present in an amount from about 0.1 to about 1.0% by weight of the total composition.

Suitable reducing agents for use in the present compositions include, but are not limited to ascorbic acid, propyl gallate and sulfites, including but not limited to sulfites, bisulfites, metabisulfites, their salts, and their derivatives. Sodium metabisulfite is one useful sulfite. Since hydroquinone has a tendency to discolor through oxidation, these reducing agents can be advantageously used because they have greater tendencies to oxidize than hydroquinone. Sodium metabisulfite has the added advantage that it does not discolor by oxidation. In hydroquinone and sodium metabisulfite compositions, it is believed that the sodium metabisulfite oxidizes first and delays the start of any oxidation of the hydroquinone, so that excessive discoloration is delayed or totally avoided. Typically, the reducing agents are present in amounts from about 0.1 to about 10% by weight of the total composition. In embodiments, the reducing agents are present in an amount from about 0.5 to about 5% by weight of the total composition.

The aqueous phase can be prepared by combining the various ingredients while mixing with heating (e.g., to 70-75° C.).

The aqueous phase is mixed with an oil phase. The oil phase can include emollients, preservatives and antioxidants.

Suitable emollients for use in the oil phase include cosmetically acceptable liquid oils. The cosmetically acceptable liquid oil is liquid at room temperature. The cosmetically acceptable liquid oil can be liquid hydrocarbon oil, liquid natural oil, liquid fatty alcohol, liquid fatty acid, liquid fatty acid ester, liquid silicone oil, and paste wax and mixtures thereof.

Non-limiting examples of the liquid hydrocarbons suitable for use in the oil phase include squalane, liquid mineral oil, and liquid polybutene. Non-limiting examples of the liquid natural oil derived from plants useful in the present compositions include almond oil, olive oil, sesame oil, safflower oil, avocado oil, cottonseed oil, jojoba oil, castor oil, soybean oil, palm kernel oil, coconut oil, and hydrogenated vegetable oil. Non-limiting examples of the liquid natural oil derived from animal sources useful in the present compositions include mink oil and egg yolk oil. Non-limiting examples of the liquid fatty alcohol useful in the present compositions are isostearyl alcohol, lanolin alcohol, oleyl alcohol, hexadecyl alcohol, octyldodecanol alcohol, linoleyl alcohol, linolenyl alcohol, lauryl alcohol and arachidyl alcohol. Fatty acid can be natural or synthetic, saturated, unsaturated, linear, or branched. Non-limiting examples of fatty acid useful in the present compositions are caprylic, isostearic, linoleic, ricinoleic, and oleic acid. Non-limiting examples of the liquid fatty acid ester useful in the present compositions are cetyl octanoate, glyceryl trioctanoate, isopropyl linoleate, isopropyl myristate, isopropyl oleate, ethyl laurate, ethyl linoleate, octyl dodecyl myristate, octyl palmitate, octyl isopelargonate, octyl dodecyl lactate, isotridecyl isononanoate, oleyl oleate, isostearyl myristate, neopentyl glycol dioctanoate, and di(capryl/capric acid) propylene glycol and mixtures thereof. Other suitable esters include triglycerides such as caprylic triglycerides, capric triglyceride, isostearic triglyceride and adipic triglyceride. Non-volatile, straight, and branched silicone oils such as dimethicone and phenyl dimethicone are also useful. Other cosmetically acceptable ingredients like sunscreens include octyl methoxy cinnamate, cinoxate, and 2-ethylphexyl p-dimethyaminobenzoate and the like.

Either one kind or two or more kinds of the cosmetically acceptable liquid oil can be used in the present compositions. Particularly useful emollients include cetyl alcohol, stearyl alcohol and combinations thereof. Typically, the emollients are present in an amount from about 5 to about 25% by weight of the total composition. In embodiments, the emollients are present in an amount from about 7.0 to about 15% by weight of the total composition.

Suitable antioxidants for use in the oil phase include, but are not limited to BHT, BHA, tocopherol, tocopheryl acetate, ascorbyl palmitate, propyl gallate, and the like. Typically, the antioxidants are present in an amount from about 0.01 to about 10% by weight of the total composition. In embodiments, the antioxidants are present in an amount from about 0.1 to about 2% by weight of the total composition.

Suitable preservatives for use in the oil phase include propylparaben, isopropylparaben, butylparaben, and isobutylparaben, and the like. The preservatives in the oil phase typically are present in an amount from about 0.01 to about 5% by weight based on the total composition. In embodiments, preservatives are present in an amount from about 0.05 to about 2% by weight based in the total composition.

The oil phase can be prepared by simply adding the ingredients for the oil phase into a tank and heating (e.g., to 70-75° C.) with moderate agitation.

The oil phase is then added to the aqueous phase (e.g., at 70-75° C.) with moderate agitation. The present hydroquinone compositions can be prepared under an inert, oxygen-free atmosphere as disclosed in U.S. Pat. No. 4,229,427 the entire disclosure of which is incorporated herein by this reference.

The tanks in which the aqueous phase and the oil phase are prepared are made from a material that does not release metallic ions into the composition. For example, a glass tank can be employed. As another example, a stainless steel tank of at least grade 316 that has been pre-treated with chelating acid to chelate metallic ions present therein can be used. Chelating can be achieved, for example, by contacting the interior of the tank with a sacrificial chelating acid. Suitable sacrificial chelating acids include citric acid, lactic acid, ascorbic acid and the like. In particularly useful embodiments, a 316 stainless steel tank is treated with a 10% citric acid solution prior to use. To prevent any further metallic ion contamination chelating agents have also been incorporated in the formula as previously described in the embodiment.

The viscosity of the final hydroquinone composition can be from about 1,000 to about 50,000 centipoise (cps). In embodiments, the viscosity of the final hydroquinone composition is from about 2,500 to about 15,000 cps. The specific gravity of the final composition can be from about 0.5 and 1.5. In embodiments, the specific gravity of the final hydroquinone is from about 0.95 to about 1.05.

In particularly useful embodiments, the final hydroquinone composition may have a substantially white color and be a semi-viscous lotion. In particularly useful embodiments, the present compositions have the ability to substantially maintain its color over time. In such embodiments, the present compositions can appear fresh, elegant and professional for their entire shelf life, ensuring patient or consumer confidence in the product.

Certain embodiments of hydroquinone compositions in accordance with this disclosure have the compositions set forth in Table 1.

TABLE 1

| Compound | % of total composition | % by weight of the total composition in Example 1 | Quantity used to produce 1,500 kg batch in Example 1 |
|---|---|---|---|
| Purified water | 65-85 | 68.32 | 1,025.7 kilograms |
| Methylparaben | 0.01-0.5 | 0.15 | 2.25 kilograms |
| Edetate disodium | 0.01-0.5 | 0.30 | 5.0 kilograms |
| Glycerin | 1-15 | 6.00 | 90.0 kilograms |
| Sodium lauryl sulfate | 0.01-5 | 1.00 | 15.0 kilograms |

TABLE 1-continued

| Compound | % of total composition | % by weight of the total composition in Example 1 | Quantity used to produce 1,500 kg batch in Example 1 |
|---|---|---|---|
| Saponins | 0.01-5 | 0.5 | 7.5 kilograms |
| Lactic Acid 88% | 0.0-5 | 1.0 | 15 kilograms |
| Cetyl alcohol | 1-25 | 8.00 | 120.0 kilograms |
| Stearyl alcohol | 0.0-25 | 1.80 | 27.0 kilograms |
| Propylparaben | 0.01-0.5 | 0.05 | 750.0 grams |
| Butylparaben | 0.00-0.5 | 0.03 | 450.0 grams |
| Tocopheryl acetate | 0.01-5 | 0.50 | 7.5 kilograms |
| BHT | 0.01-0.5 | 0.05 | 750.0 grams |
| Ascorbic Acid | 0.01-5 | 1.5 | 22.5 kilograms |
| Sodium metabisulfite | 0.01-5 | 0.7 | 10.5 kilograms |
| Hydroquinone + 1% OVR | 0.1-10 | 4.04 | 60.6 kilograms |
| Octyl Methoxycinnamate | 0.0-8.00 | 3.00 | 45 kilograms |
| Oxybenzone | 0.0-8.00 | 3.00 | 45 kilograms |
| TEA-salicylate | 0.0-5 | | |
| PPG-2 myristyl ether propionate | 0.0-5 | | |
| phenyl trimethicone | 0.0-5 | | |

The composition can be packaged in suitable containers such as tubes or bottles. Suitable containers are commercially available from a variety of suppliers. A wide variety of containers and suppliers are listed in the CPC Packaging Directory. (See, Buyers' Guide under "Containers" at www-.cpcpkg.com).

Testing Methodology

A stability program was developed to ensure that any product manufactured retained within the specified limits and throughout the period of storage and use, the similar properties and characteristics that it possessed at the time of its manufacture as reported in Table 2 below.

The stability program consisted of accelerated, 9α and long term testing studies. Data collected from the studies determined the shelf life or expiration date of the product. Throughout the study, side or inverted orientation was used for the storage of bottles. The accelerated testing was done by subjecting the product at 40° C.±2° C., 75%±5% relative humidity for one month, two months, and three months. The long term testing was done by subjecting the product at 25° C.±2° C. ambient temperature at intervals of 3, 12, 24, 36, 48 and 60 months. The 9α testing was done by subjecting the product at 40° C. for 3 months, then moving sample to 25° C. for 6 months and then pulling for testing.

Variations of the accelerated testing were chosen for suspensions, topical cream, and ointments. This is called the freeze/thaw challenge test. Products were subjected to 4 (four) cycles. Each cycle entails 6 (six) days at −15° C. and 1 (one) day at controlled room temperature.

Products tested were packaged in the container/closure system in which they are to be marketed. In the case where more than one container/closure system was used for a particular size, testing was done on each container closure system. When the same resin was used for different size container for the same product, only the largest and the smallest size containers were subjected to stability testing for that product. If package 1 (pk1) was of different resin than package 2 (pk2), pk2 was subjected to all tests as pk1.

The pilot batch or the R&D batches were placed on accelerated stability and the first three production batches of a formulation were packaged for each container/closure system placed on full stability testing. Yearly thereafter, one production batch was added to the stability program.

Cosmetic products were subjected to accelerated testing, and retain samples were randomly checked.

Results

The results of various stability studies on a formulation of table 1 in accordance with this disclosure are reported in Table 2 below.

before use and all formulations and intermediate formulations were degassed. The hydroquinone-containing formulation was transferred to storage containers that were purged with nitrogen both before and after filling.

While several embodiments of the disclosure have been described, it is not intended that the disclosure be limited thereto, as it is intended that the disclosure be as broad in scope as the art will allow and that the specification be read

TABLE 2

| | Appearance | | | Viscosity | | | pH | | | Hydroquinone (4% Label claim) | | | | | |
| --- | --- | --- | --- | --- | --- | --- | --- | --- | --- | --- | --- | --- | --- | --- | --- |
| | | | | | | | | | | Begin | | Middle | | End | |
| | Begin | Middle | End | | | | | | | | % of | | % of | | % of |
| | Pass/ | Pass/ | Pass/ | Begin | Mid | End | | | | | Label | | Label | | Label |
| Conditions | Fail | Fail | Fail | cps | cps | cps | Begin | Mid | End | Assay | Claim | Assay | Claim | Assay | Claim |
| Initial Bulk | Pass | Pass | Pass | 16,000 | 16,000 | 15,500 | 3.37 | 3.36 | 3.31 | 3.852 | 96.0 | 3.877 | 97.0 | 3.950 | 99.0 |
| 1 Month 40° C., 75% RH | Pass | Pass | Pass | 16,000 | 16,250 | 13,500 | 2.90 | 3.05 | 3.18 | 4.110 | 102.8 | 4.115 | 102.9 | 4.118 | 103.0 |
| 1 Month 30° C., 60% RH | Pass | Pass | Pass | 13,500 | 16,000 | 13,500 | 3.05 | 3.13 | 3.17 | 4.074 | 101.9 | 4.117 | 102.9 | 4.096 | 102.4 |
| 2 Month 40° C., 75% RH | Pass | Pass | Pass | 15,500 | 15,000 | 12,500 | 3.01 | 3.15 | 3.14 | 3.905 | 97.6 | 3.884 | 97.1 | 3.947 | 98.7 |
| 2 Month 30° C., 60% RH | Pass | Pass | Pass | 13,000 | 15,000 | 13,250 | 3.01 | 3.09 | 3.10 | 3.883 | 97.1 | 3.888 | 97.2 | 3.809 | 95.2 |
| 3 Month 40° C., 75% RH | Pass | Pass | Pass | 18,000 | 17,250 | 17,000 | 2.84 | 2.41 | 2.49 | 4.026 | 100.7 | 3.972 | 99.3 | 4.022 | 100.6 |
| 3 Month 30° C., 60% RH | Pass | Pass | Pass | 12,500 | 12,500 | 12,500 | 2.76 | 2.75 | 2.84 | 4.047 | 101.2 | 4.049 | 101.2 | 3.980 | 99.5 |
| 3 Month Bulk | Pass | Pass | Pass | 12,500 | 13,000 | 12,500 | 3.33 | 3.23 | 3.31 | 3.891 | 97.3 | 3.920 | 98.0 | 3.888 | 97.2 |
| 9 Alpha 25° C., 60% RH* | Pass | Pass | Pass | 17,000 | 16,750 | 16,500 | 2.42 | 2.36 | 2.35 | 3.836 3.827 | 96.0 96.0 | 3.861 3.885 | 96.0 97.0 | 3.866 3.889 | 97.0 97.0 |
| 12 Month 25° C., 60% RH* | Pass | Pass | Pass | 13,000 | 13,250 | 13,500 | 3.15 | 3.21 | 3.09 | 3.921 3.908 | 98.0 97.7 | 3.904 3.872 | 97.6 97.3 | 3.917 3.942 | 97.9 98.6 |
| 24 Month 25° C., 60% RH* | Pass | Pass | Pass | 19,500 | 19,000 | 19,00 | 2.11 | 2.07 | 2.08 | 3.86 3.86 | 96.5 96.5 | 3.90 3.91 | 97.5 97.8 | 3.93 3.91 | 98.2 97.8 |
| 3 mos, 40° C., 75% RH Then 25° C., 60% RH for 27 mos* | Pass | Pass | Pass | 20,000 | 20,000 | 20,000 | 2.01 | 2.01 | 2.01 | 3.82 3.84 | 95.5 96.0 | 3.83 3.85 | 9.8 96.2 | 3.84 3.82 | 96.0 995.5 |
| 3 mos, 40° C., 75% RH then 25° C., 60% RH for 28 months* | Pass | Pass | Pass | 13,000 | 13,000 | 13,000 | 1.95 | 1.95 | 1.95 | 3.99 3.96 | 99.8 99.0 | 4.02 4.02 | 100.5 100.5 | 4.02 3.99 | 100.5 99.8 |

*Assay results reported for two samples

EXAMPLE I 1025.7 Kg of purified water was added to a premix tank under nitrogen gas. The premix tank was a jacketed and covered 316 stainless steel tank that had been pre-treated with a 10% citric acid solution. The following water phase ingredients were added under gentle heat to make a 1500 Kg sample. All solids were homogenously dispersed by mixing at about 70-75° C.: 2.25 Kg of methylparaben, 5.0 Kg of edetate disodium, 90 KG glycerin, 15 Kg SLS, 7.5 Kg saponins, 15 Kg lactic acid 88%, 22.5 Kg ascorbic acid, 10.5 Kg sodium metabisulfite, 60.6 Kg hydroquinone (includes 1% overage). The following oil phase ingredients were mixed in a 316 stainless steel tank that had been pre-treated with a 10% citric acid solution at about 70-75° C.: 120 Kg cetyl alcohol, 27 Kg stearyl alcohol, 750 g propylparaben, 450 g butyl paraben, 7.5 Kg tocopheryl acetate, 45 Kg oxybenzone, 45 Kg octyl methoxycinnamate and 750 g BHT. All contents were then transferred under nitrogen gas into a jacketed and covered 316 stainless steel tank that had been pre-treated with a 10% citric acid solution where the oil phase and water phase were mixed and cooled in order to form an emulsion. All solvents were degassed with nitrogen likewise. Therefore, the above description should not be construed as limiting, but merely as exemplifications of embodiments. Those skilled in the art will envision other modifications within the scope and spirit of the claims appended hereto.

What is claimed is:

1. A method comprising:
   (a) passivating a stainless steel tank to chelate metallic ions therein, thereby preparing a passivated tank; and then
   (b) preparing an emulsion containing hydroquinone, a preservative, a chelating agent, an emulsifier, a humectant, a pH adjuster, an antioxidant, an emollient, and a reducing agent in the passivated tank of step (a), wherein the discoloration of the emulsion is slowed compared to the discoloration of the same emulsion that has not been prepared in the passivated tank.

2. The method of claim 1, wherein passivating the stainless steel tank comprises contacting the stainless steel tank with a chelating acid.

3. The method of claim 2, wherein the chelating acid is citric acid.

4. The method of claim 1, wherein the preservative is a member selected from the group consisting of benzoic acid, benzyl alcohol, butylparaben, diazolidinyl urea, 2,3-Imidazolidinedione, isopropylparaben, isobutylparaben, methylparaben, propylparaben, sodium butylparaben, sorbic acid, and combinations thereof.

5. The method of claim 1, wherein the chelating agent is a member selected from the group consisting of citric acid, edetate disodium, ethylenediaminetetraacetic acid, etidronic acid sodium dihydroxyethylglycinate, nitrilotriacetic acid, and combinations thereof.

6. The method of claim 1, wherein the emulsifier is a member selected from the group consisting of cetearyl alcohol, ethoxylated fatty alcohols, PEG-1000 monocetyl ether, alkyl trimethyl ammonium bromide, polyol ester glycerol monostearate, potassium stearate, sodium lauryl sulfate, sodium cetearyl sulfate, saponins, and combinations thereof.

7. The method of claim 1, wherein the humectant is a member selected from the group consisting of glycerin, diglycerin, triglycerin, polyglycerin, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, ethylene glycol monoalkyl ether, diethylene glycol monoalkyl ether, glucose, maltose, sucrose, lactose, xylitose, xylitol, sorbitol, mannitol, maltitol, panthenol, pentaerythritol, hyaluronic acid, and combinations thereof.

8. The method of claim 1, wherein the pH adjuster is a member selected from the group consisting of citric acid, phosphoric acid, lactic acid, glycolic acid, and combinations thereof.

9. The method of claim 1, wherein the antioxidant is a member selected from the group consisting of ascorbyl palmitate, 2,6 ditertiarybutyl-4-methyl phenol, butylated hydroxyanisole, tocopherol, tocopheryl acetate, propyl gallate, and combinations thereof.

10. The method of claim 1, wherein the emollient is a member selected from the group consisting of cetyl alcohol, stearyl alcohol, liquid hydrocarbon oil, liquid natural oil, liquid fatty alcohol, liquid fatty acid, liquid fatty acid ester, liquid silicone oil, paste wax, and combinations thereof.

11. The method of claim 10, wherein the liquid hydrocarbon oil is a member selected from the group consisting of squalane, liquid mineral oil, liquid polybutene, and combinations thereof.

12. The method of claim 10, wherein the liquid natural oil is a member selected from the group consisting of almond oil, olive oil, sesame oil, safflower oil, avocado oil, cottonseed oil, jojoba oil, castor oil, soybean oil, palm kernel oil, coconut oil, hydrogenated vegetable oil, mink oil, egg yolk oil, and combinations thereof.

13. The method of claim 10, wherein the liquid fatty alcohol is a member selected from the group consisting of isostearyl alcohol, lanolin alcohol, oleyl alcohol, hexadecyl alcohol, octyldodecanol alcohol, linoleyl alcohol, linolenyl alcohol, lauryl alcohol, arachidyl alcohol, and combinations thereof.

14. The method of claim 10, wherein the liquid fatty acid is a member selected from the group consisting of caprylic acid, isostearic acid, linoleic acid, ricinoleic acid, oleic acid, and combinations thereof.

15. The method of claim 10, wherein the liquid fatty acid ester is a member selected from the group consisting of cetyl octanoate, glyceryl trioctanoate, isopropyl linoleate, isopropyl myristate, isopropyl oleate, ethyllaurate, ethyl linoleate, octyl dodecyl myristate, octyl palmitate, octyl isopelargonate, octyl dodecyllactate, isotridecyl isononanoate, oleyl oleate, isostearyl myristate, neopentyl glycol dioctanoate, and di(capryl/capric acid) propylene glycol, and combinations thereof.

16. The method of claim 1, wherein the reducing agent is a member selected from the group consisting of ascorbic acid, propyl gallate, sodium metabisulfite, and combination thereof.

17. The method of claim 1, wherein the emulsion comprises a viscosity of from about 1,000 to about 50,000 centipoise.

18. The method of claim 1, further comprising adding a sunscreen.

19. The method of claim 1, wherein the emulsion is a lotion.

20. The method of claim 1, wherein the emulsion maintains an acceptable color for three years.

21. The method of claim 20, wherein the acceptable color is a color lighter than brown.

22. A method for preparing a topical hydroquinone composition, the method comprising:
preparing an emulsion containing hydroquinone, a preservative, a chelating agent, an emulsifier, a humectant, a pH adjuster, an antioxidant, an emollient and a reducing agent in a passivated stainless steel tank, wherein the stainless steel tank is passivated prior to preparing the emulsion in the stainless steel tank;
wherein the discoloration of the emulsion is slowed compared to the discoloration of the same emulsion that has been prepared in a non-passivated tank.

* * * * *